United States Patent [19]

Michelson

[11] Patent Number: 5,026,386
[45] Date of Patent: Jun. 25, 1991

[54] FLAVAL SEPARATOR

[76] Inventor: Gary K. Michelson, 438 Sherman Canal, Venice, Calif. 90291

[21] Appl. No.: 289,258

[22] Filed: Dec. 23, 1988

[51] Int. Cl.⁵ .............................................. A61B 17/32
[52] U.S. Cl. ...................................... 606/170; 30/137
[58] Field of Search ............... 606/167, 170, 160, 161, 606/84; 30/113, 120.1, 324, 346, 124, 132, 123.7

[56] References Cited

U.S. PATENT DOCUMENTS

| | | | |
|---|---|---|---|
| 1,672,816 | 6/1928 | Kohr | 606/161 |
| 2,521,161 | 9/1950 | Groyer | 606/167 |
| 2,677,843 | 5/1954 | Goodman | 606/160 |
| 3,367,335 | 2/1968 | Ward et al. | 606/167 |
| 3,885,271 | 5/1975 | Kollander | 30/136 |
| 4,800,896 | 1/1989 | Jalowayski | 606/161 |

Primary Examiner—C. Fred Rosenbaum
Assistant Examiner—William Lewis
Attorney, Agent, or Firm—Lewis Anten

[57] ABSTRACT

A surgical instrument specifically designed to facilitate the separation of the Ligamentum Flavum from its vertebral attachments is disclosed. The instrument has an angulated semispherical solid ovoid tip with sharp edges along its top flat surface.

4 Claims, 2 Drawing Sheets

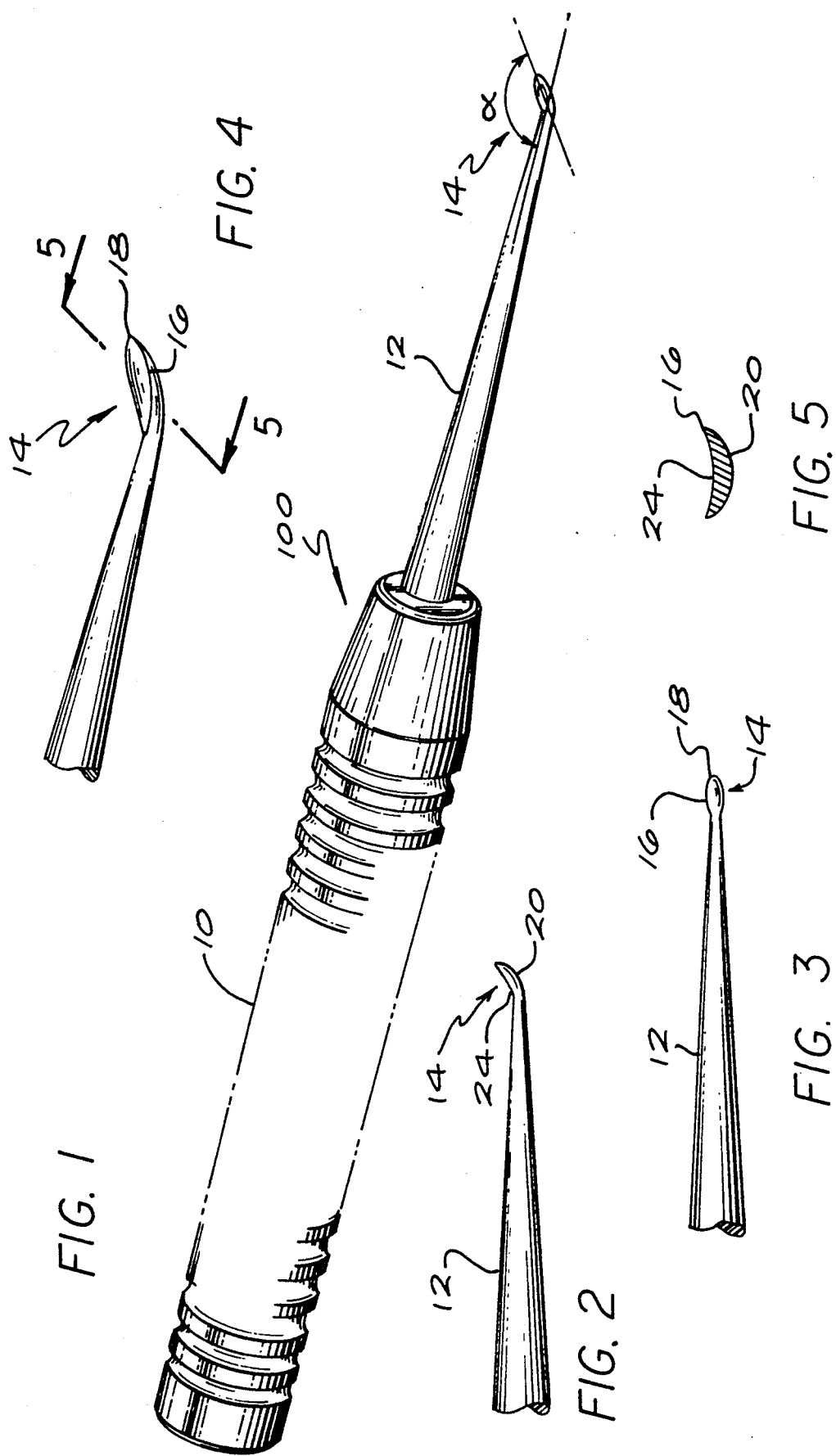

FLAVAL SEPARATOR

BACKGROUND

By far performed spinal surgery is a lumbar laminectomy, which is frequently combined with a discectomy, fusion, or both. A laminectomy entails the removal of a portion of bone from the lamina from the posterior aspect of the spine to gain entrance into the spinal canal which contains the neural elements, and to provide access to the disc.

It is therefore necessary to separate the flavum from the lamina prior to removal of the bone. However, this task is complicated by the fact that the inferior laminar surface is neither straight nor flat. Therefore, if an attempt is made to separate the flavum from the bone with a flat edged instrument, such an instrument will get into the substance of the ligament causing delamination within the ligament, and without achieving the desired separation of the ligament from the lamina. This problem is compounded by the fact that while the Ligamentum Flavum is very fibrous and strong, immediately beneath it is the extremely delicate and vulnerable dural sac and the nerve roots. Surgeons have, while attempting to separate the flavum from the lamina, inadvertently plunged through into the spinal canal, rupturing the dural sac and causing neural injury.

The laminar bone is usually removed by using an up biting rongeur. However, the Ligamentum Flavum (literally yellow ligament) is extremely thick and is a firmly attached sheet of fibrous tissue running from the underside of one lamina to the underside of the next. The flavum acts as a significant impediment to the placement of the foot portion of the rongeur beneath the laminar bone to be removed.

The problem with this approach is that the rongeur foot has not been configured for this purpose and so significant force is required making that maneuver dangerous. Since the tip of the rongeur disappears from view as it is pushed under the lamina, one cannot tell if the rongeur, when closed, will bite bone alone, bone plus flavum, or if the tip has gone beyond the attachment of the flavum thus grasping the bone plus dural sac and nerve roots.

Another way to separate the flavum, presently in use, is by dissectors. Dissectors are strips of metal with edges that may be sharp or dull and whose overall configurations can be relatively straight along the longitudinal axes or which may have anywhere from a slight to a more pronounced curve or even be acutely angled such as a dental tool. As per the previous discussion, as these instruments have not been specifically designed for this specific purpose, they tend to either dig into the substance of the Ligamentum Flavum or to risk perforating the dural sac beneath.

Another group of instruments that are used are currettes. These surgical instruments have a handle and a shaft and terminate in an tip resembling a small cup. These instruments are primarily intended to be used for scooping out material, e.g. disc, or bone and are therefore sharpened along the inner wall of a cup so as to facilitate the cup's being filled as it passes through the tissue. As currettes are designed to have cups and to be sharpened in such a manner so as to facilitate the filling of those cups, they are really not appropriate for removing the flavum as the flavum is most effectively and safely removed as a sheet rather than in small cupful bits. Some surgeons attempt to use various currettes as side cutting knives beneath the lamina. This is ineffective because they are not capable of being sharpened in such a way as to facilitate this maneuver, and more importantly, because they are designed to hold tissue the cups have considerable depth in relation to their other dimensions such that if a curette were large enough to correspond to the extent of the flaval attachment, then its overall thickness would potentially pose a threat to the underlying nerves and dural sac which would be compressed or crushed.

There is therefore a need for an instrument specifically designed for the task of removing this flavum from the lamina and the use of which would be in such a manner as to safeguard the sanctity of the underlying neural contents.

Objects of the Present Invention

It is an object of the present invention to provide for a surgical instrument that is specifically designed to separate the Ligamentum Flavum from the undersurface of the lamina more efficiently;

It is another object of the present invention to provide for a surgical instrument for separating the Ligamentous Flavin from the undersurface that is more effective.

It is yet another object of the present invention to provide for a surgical instrument for separating the Ligamentous Flavin which performs quicker and safer.

These and other objects of the present invention will be evident from review of the following specification and the accompanying drawings.

SUMMARY OF THE INVENTION

The present invention comprises a surgical instrument that is, because of its unique shape and configuration, able to always present to the undersurface of the lamina a sharp edge and which has a variable degree of curvature so as to always maximize the congruency of the blade edge to the under surface of the lamina.

The basic configuration of the instrument is half an ovoid having a flat top surface with sharpened edges. Because of its almost flat top surface and curved side surfaces, the present invention is able to rotate to, and only to, that point where the instrument tip edge substantially conforms to the laminar profile.

The tip of the instrument is able to displace the Ligamentum Flavum all at one time, as an intact sheet, while keeping it interposed above the dural sac, thereby being safer than the prior art devices.

BRIEF DESCRIPTION OF THE DRAWINGS

FIG. 1 is a perspective view of the instrument of the present invention.

FIG. 2 is a side view of the tip portion of the present invention.

FIG. 3 is a top view of the tip of the present invention.

FIG. 4 is an enlarged perspective drawing of the tip of the present invention.

FIG. 5 is a side section view of the tip of the present invention taken along lines 5—5 of FIG. 4.

DETAILED DESCRIPTION OF THE DRAWINGS

Figure 6:
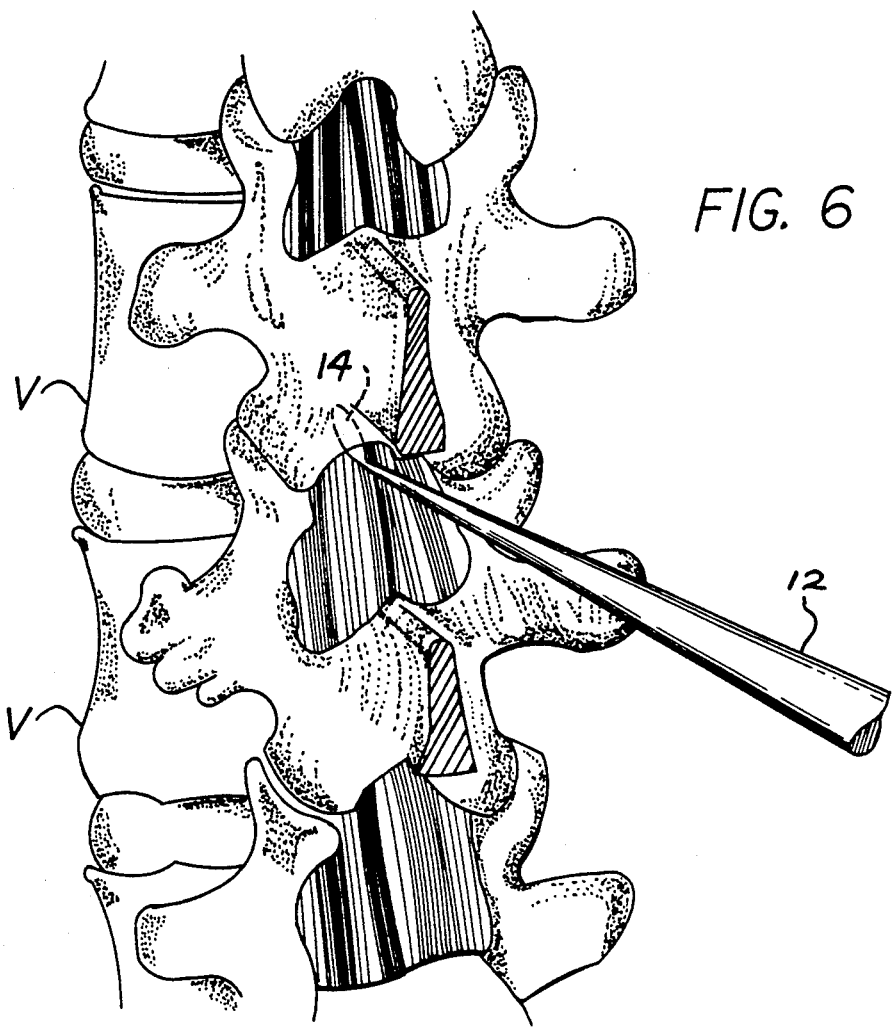
FIG. 6 is a perspective view of the tip of the present invention in use, separating the Ligamentum Flavum from the undersurface of the vertebral lamina.

Referring to FIGS. 1-5, the flaval separator 100 of the present invention is show. The instrument consists of a handle 10 and a cylindrical tapered shaft 12 along the central axis of the handle 10 and rigidly attached to the handle by conventional means such as by screws and nuts as shown. The tapered end of the shaft 12 terminates in a tip 14. In the preferred embodiment the main axis of the tip 14 is at an angle of approximately 120 degrees to the central axis of the shaft 12, although it may be as much as 160 degrees or as little as 90 degrees.

The tip 14 has a sharpened perimeter 16, a pointed front tip 18, and a rounded ovoid shape bottom surface 20. Except for a slight concavity 22, to allow for the sharpened edge 16, the upper surface 24 of the tip is substantially flat. As more clearly shown in FIG. 5 the perimeter 16 of the tip 14 is curved along the side walls with the radius of curvature constantly changing.

Figure 7:
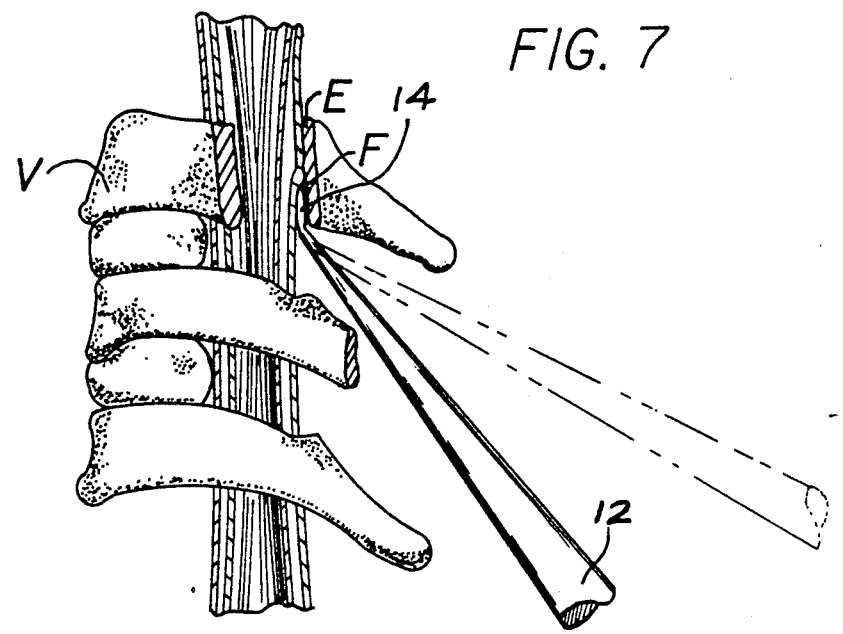
FIG. 7 is a side view of the tip of the present invention being used to push away the Ligamentum Flavum and to remove laminar bone.

FIG. 6 and 7 illustrate the flaval separator of the present invention 100 in use. The tip 14, is aligned between the interior laminar edge E and the flavum F. The angle of the tip 14 allows the shaft 12 to be well positioned and the handle 10 to lie clear of the wound. It can be seen that the sharp edge 16 of the tip 14 is aligned and congruent to the inferior laminar surface so as to facilitate the separation of the flavum from the bone while the rounded bottom 20 clears the flavum which remains interposed above the dura D and acts as a protector. By rotating the tip 14 slightly until the sharp edge 16 of the tip 14 conforms to the laminar profile, and sliding the tip forward, the entire flavum may be separated from the bone.

While the present invention has been described with regards to the preferred embodiment, it is understood that variation to the present invention may be made without departing from the concept of the present invention. For example, the angle of the tip or the size of the tip may vary, without departing from the inventive concept disclosed herein.

What is claimed is:

1. A surgical instrument comprising a shaft, said shaft having a tip attached to said shaft at an angle less than 180 degrees, said tip being generally oval in shape and having a substantially flat top surface and a convex bottom surface, said top surface having a smooth sharp edge around its perimeter.

2. The surgical instrument of claim 1 in which the angle formed between said top surface of said tip and said shaft is approximately 120 degrees.

3. The surgical instrument of claim 1 in which the angle formed between said top surface of said tip and said shaft is between approximately 160 degrees and 90 degrees.

4. The surgical instrument of claim 1 in which said top surface is lower than said edge sufficient to permit forming said sharp edge around the perimeter of said tip.

* * * * *